United States Patent [19]

Berardini

[11] Patent Number: 4,654,198

[45] Date of Patent: Mar. 31, 1987

[54] DYNAMIC AIR DEFLECTOR

[76] Inventor: John R. Berardini, 147 Medhurst Dr., Nepean, Ontario, Canada, K2G 4J9

[21] Appl. No.: 792,004

[22] Filed: Oct. 28, 1985

Related U.S. Application Data

[63] Continuation-in-part of Ser. No. 674,932, Nov. 26, 1984, abandoned.

[30] Foreign Application Priority Data

Feb. 13, 1984 [CA] Canada .................... 447317

[51] Int. Cl.[4] ............................................. F24F 3/12
[52] U.S. Cl. ...................................... 422/124; 98/105
[58] Field of Search ................. 98/101, 103, 105, 108, 98/109; 422/122, 123, 124

[56] References Cited

U.S. PATENT DOCUMENTS

| 526,653 | 9/1894 | Iliowizi | 98/105 X |
| 725,086 | 4/1903 | Jacobs | 422/124 |
| 1,246,529 | 11/1917 | Bieder | 422/124 |
| 1,581,243 | 4/1926 | Stoeber | 98/109 |
| 2,014,773 | 9/1935 | Matteson | 422/124 X |
| 3,902,877 | 9/1975 | Swaim | 422/123 X |

FOREIGN PATENT DOCUMENTS

| 94443 | of 1923 | Austria | 422/124 |
| 18684 | of 1896 | United Kingdom | 98/39 |

Primary Examiner—Harold Joyce

[57] ABSTRACT

An air deflector can be mounted on an air register. The deflector has a sloping rear wall and a pair of side walls. The two side walls have opposed holes which support a perforated, finned roller rotatable about a horizontal axis. The roller has six horizontally curved fins spaced equally apart with perforations above them. The rear wall defines with the roller a flow path extending through the deflector sets the roller in rotation and is thereby projected out of the top of the deflector at an increased velocity and over a greater distance into the room. A solid circular stick of deodorizer can be internally located within the finned roller.

9 Claims, 3 Drawing Figures

4,654,198

DYNAMIC AIR DEFLECTOR

This is a Continuation-in-part of application Ser. No. 674,932 filed Nov. 26, 1984, now abandoned.

BACKGROUND OF THE INVENTION

This invention relates to an air deflector adapted to be mounted over a register in a forced air heating or air conditioning system.

It is common practice to mount an air deflector over a register in a heating or air conditioning system. The deflector usually comprises a transparent plastic housing with a pair of side walls and a curved rear wall that re-directs the upwardly flowing air coming from the register laterally into the room. A simple static deflector of this type is inefficient as the air, being at a relatively low pressure, is not projected with any force into the room and in the case of warm air quickly rises to the ceiling, where its warmth cannot be utilized.

A static air deflector also has no provision for reducing any odors in the outflowing air.

SUMMARY OF THE INVENTION

An object of the invention is to alleviate the aforementioned disadvantages.

Accordingly, the present invention provides an air deflector comprising a housing having a pair of laterally spaced, vertical side walls and a sloping rear deflector wall, said housing having an open bottom for mounting over an air register and an open front extending to the bottom of the housing for discharging air into a room, and a roller mounted in said open front for rotation about a horizontal axis between said side walls, said roller having a plurality of circumferentially equispaced fins extending therealong, each fin being curved radially outwardly such that in its uppermost position it defines a concave surface facing towards the rear, said rear deflector wall defining with the roller a flow path extending over the top of the roller, whereby the roller is set in rotation by the air flow to project air out of the top of the deflector at an increased velocity and thereby over a greater distance into the room.

In a preferred embodiment, the roller is hollow with perforations along its length and a solid deodorizer, such as a deodorizer stick mounted inside.

Such a deflector fills a room with cool or warm air more evenly and efficiently. Instead of the air flowing nearly straight upwards, the deflector maintains air flow across the room. The deodorizer can be added as an added benefit for personal use. Deodorized, heated or cooled air can then be expelled to any specific area of the room.

The deflector should be placed on the register to direct the air where required. Magnets on the bottom enable the deflector to be mounted on any air register in the correct manner, with virtually no air escaping from the sides.

The deflector according to the invention also propels air out faster and farther than the static deflector of the prior art.

This action can result in quicker heating or cooling and a saving on furnace/air conditioning units and expenses. The provision of the deodorizer in the rotating roller is a particularly effective way of deodorizing the outflowing air.

DESCRIPTION OF THE PREFERRED EMBODIMENT

Figure 1:
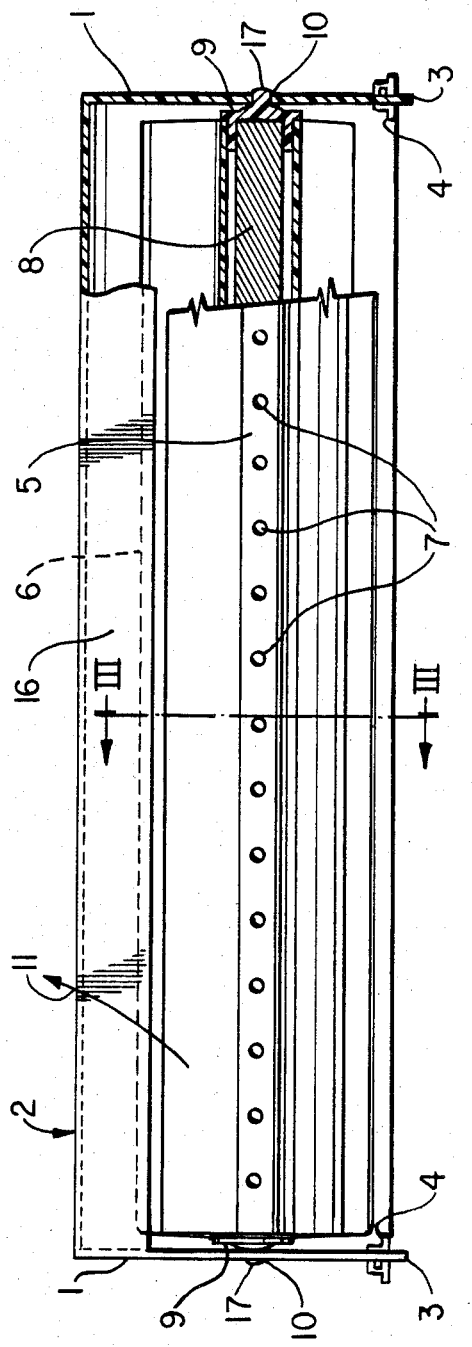
FIG. 1 is an elevation partly in section of one embodiment.
Figure 3:
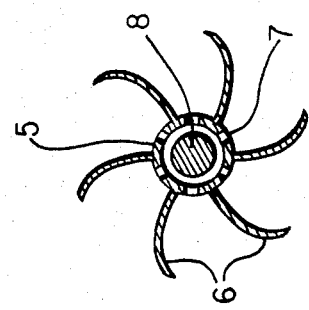
FIG. 3 is a section of line III—III of FIG. 1.
Figure 2:
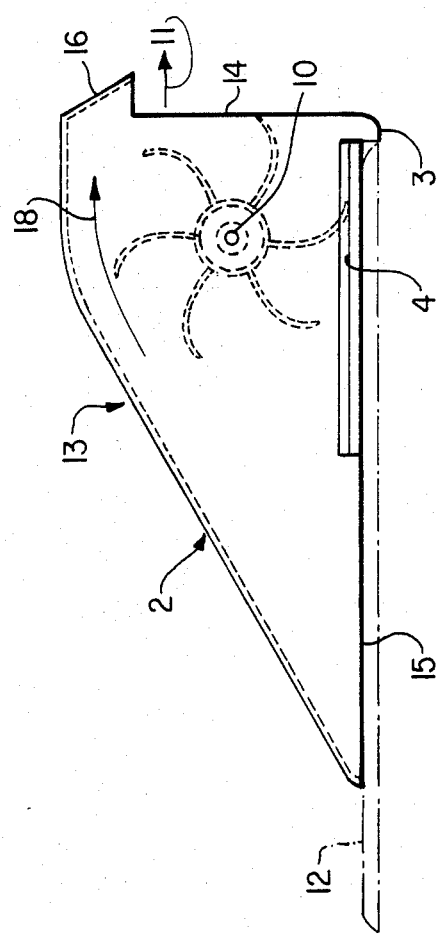
FIG. 2 is a side plan view of this embodiment.

In the drawings, the air deflector comprises a housing with an open bottom 15 adapted to be fitted over an air register 12 of a forced air heating/air conditioning system and an open front 14 for projecting air into a room. The housing 13 has two side walls 1 and a sloping rear deflector wall 3 terminating at its forward end in forwardly and downwardly inclined lip 16 extending over the front of the housing 1. Magnets 4 are attached to the lower edges of side walls 1 to magnetically hold the housing on the air register 12. The side walls 1 also have protrusions 3 to locate the deflector properly at the front of the air register 12.

Hollow roller 5, which has six equally spaced curved fins 6, with the uppermost fins concave towards the rear, is mounted for rotation about a horizontal axis between side walls 1. For this purpose, stub shafts 17 are mounted in opposed holes 10 in the side walls 1.

Roller 5 has perforations 7 for releasing deodorized scent from an internal stick of deodorant 8. Deodorant stick 8 is held in place by end caps 9 on the roller. End caps 9 are glued to the ends of roller 5 and include the stub shafts 17. The roller 5 rotates freely about its horizontal axis.

In operation, air enters the housing from the register 12 through the open bottom 15 and is deflected forwardly by the sloping rear wall 2 before striking the roller. The air sets the roller in clockwise rotation, flowing over the top of the roller as shown by arrow 18 and out through the front of the housing to be projected laterally into the room at increased velocity. The lip 16 serves to confine the flow path around the top of the roller and increases the efficiency of the unit.

The presence of the roller greatly increases the velocity of the air coming out of the deflector and therefore the distance over which the air is projected into the room. The roller reduces the effective size of the front opening of the housing, thus increasing the air flow velocity, but without introducing the flow resistance that would be caused by a simple restriction in the opening.

The housing 13 is made of resilient plastic to enable the roller to be readily replaced by a new roller containing a fresh deodorizing stick by merely forcing apart the side walls.

The embodiments of the invention in which an exclusive property or privilege is claimed are defined as follows:

1. An air deflector comprising a housing having a pair of laterally spaced, vertical side walls and a sloping rear deflector wall, said housing having an open bottom for mounting over an air register and an open front extending to the bottom of the housing for discharging air into a room, and a roller mounted in said open front for rotation about a horizontal axis between said side walls, said roller having a plurality of circumferentially equispaced fins extending therealong, each fin being curved radially outwardly such that in its uppermost position it defines a concave surface facing towards the rear and in its lowermost position it extends substantially to the bottom of the housing, said rear deflector wall extending over the top of the roller and being spaces therefrom to define with the roller a flow path extending over the top of the roller, whereby the roller is set in rotation by the air flow passing thereover to project air out of the top of the deflector at an increased velocity and thereby over a greater distance into the room.

2. An air deflector according to claim 1, further comprising a depending lip along a top edge of the front of the housing and spaced from the roller to confine the flow path extending over the top of the roller.

3. An air deflector according to claim 2, wherein said depending lip is inclined forwardly and downwardly from said top edge.

4. An air deflector according to claim 1, wherein each said side walls have opposed holes formed therein and the finned roller has stub shafts mounted in said holes.

5. An air deflector according to claim 4, wherein said finned roller is closed at the ends by end caps including said stub shafts.

6. An air deflector according to claim 5, wherein said roller has perforations along its length between said fins and said roller contains a deodorant.

7. An air deflector according to claim 6, wherein an internal solid stick of deodorizer, held in place by said end caps, is fitted within said roller.

8. An air deflector according to claim 6, wherein said roller is interchangeable.

9. An air deflector comprising a housing having a pair of laterally spaced, vertical side walls and a sloping rear deflector wall, said housing having an open bottom for mounting over an air-register and an open front extending to the bottom of the housing for discharging air into a room, and a roller mounted in said open front for rotation about a horizontal axis between said side walls, said roller having a plurality of circumferentially equi-spaced fins extending there along, each fin being curved radially outwardly such that in its uppermost position it defines a concave surface facing towards the rear, and each said side walls have opposed holes formed therein and the fin roller has stub shafts mounted in said holes, said finned roller is closed at the ends by end-caps including said stub shafts and said roller has perforations along its length between said fins, an internal solid stick of deodorizer, held in place by said end caps, is fitted within said roller, and said rear deflector wall extends over the top of the roller and is spaced therefrom to define with the roller a flow path extending over the top of the roller, whereby the roller is set in rotation by the air flow passing thereover to project deodorized air out of the top of the deflector at an increased velocity and thereby over a greater distance into the room.

* * * * *